US012655143B2

(12) United States Patent
Heinrich et al.

(10) Patent No.: US 12,655,143 B2
(45) Date of Patent: Jun. 16, 2026

(54) PROCESS FOR PREPARING AN ACTIVIN RECEPTOR-LIKE KINASE INHIBITOR

(71) Applicant: Blueprint Medicines Corporation, Cambridge, MA (US)

(72) Inventors: Brian Heinrich, Cambridge, MA (US); Gordon Wilkie, Cambridge, MA (US); Dominik Siegel, Dottikon (CH); Harald Ohmer, Dottikon (CH)

(73) Assignee: Blueprint Medicines Corporation, Cambridge, MA (US)

( * ) Notice: Subject to any disclaimer, the term of this patent is extended or adjusted under 35 U.S.C. 154(b) by 1102 days.

(21) Appl. No.: 17/765,755

(22) PCT Filed: Oct. 2, 2020

(86) PCT No.: PCT/US2020/053904
§ 371 (c)(1),
(2) Date: Mar. 31, 2022

(87) PCT Pub. No.: WO2021/067670
PCT Pub. Date: Apr. 8, 2021

(65) Prior Publication Data

US 2022/0396576 A1 Dec. 15, 2022

Related U.S. Application Data

(60) Provisional application No. 62/909,533, filed on Oct. 2, 2019.

(51) Int. Cl.
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
None
See application file for complete search history.

(56) References Cited

U.S. PATENT DOCUMENTS 10,233,186 B2 3/2019 Brooijmans et al.
2017/0298069 A1* 10/2017 Brooijmans ............ A61P 43/00

FOREIGN PATENT DOCUMENTS

| | | | | |
|---|---|---|---|---|
| CN | 1192214 | A | | 9/1998 |
| CN | 109311889 | A | | 2/2019 |
| EA | 020847 | B1 | | 2/2015 |
| WO | 1996/40684 | A1 | | 12/1996 |
| WO | WO 1996040684 | A1 | * | 12/1996 |
| WO | 2017/181117 | A1 | | 10/2017 |

OTHER PUBLICATIONS

Luzung et al., A Mild Cross-Coupling of 2-Heterocyclic Organozinc Reagents and Aryl Chlorides. Journal of Organic Chemistry. 2010;75(23):8330-8332.
International Search Report and Written Opinion for Application No. PCT/US2020/053904, dated Dec. 1, 2020, 10 pages.

* cited by examiner

*Primary Examiner* — Clinton A Brooks
*Assistant Examiner* — Nicola Maria Bauer
(74) *Attorney, Agent, or Firm* — McCarter & English, LLP; Wei Song

(57) ABSTRACT

The present disclosure provides a method of preparing a compound represented by formula (I). The method comprises reacting in a reaction mixture a first starting material represented by formula (II) and a second starting material represented by formula (III) under Negishi conditions: to form the compound of formula (I). R is an amine protecting group; Y is Cl, Br or I; and Z is triflate, Cl, Br or I.

(I)

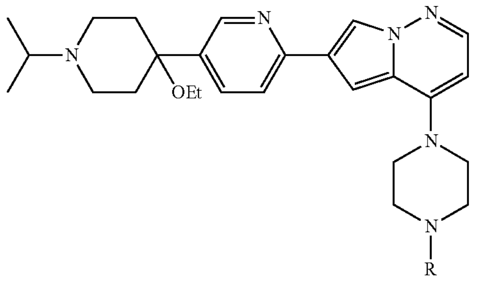

(II)

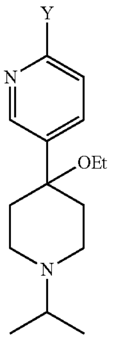

(III)

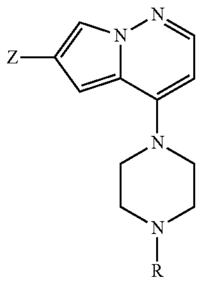

27 Claims, 2 Drawing Sheets

PROCESS FOR PREPARING AN ACTIVIN RECEPTOR-LIKE KINASE INHIBITOR

CROSS-REFERENCE TO RELATED APPLICATIONS

This application is a 35 U.S.C. § 371 national stage filing of International Application No. PCT/US2020/053904, filed on Oct. 2, 2020, which claims priority from U.S. Provisional Application No. 62/909,533, filed Oct. 2, 2019. The entire contents of the aforementioned application are incorporated herein by reference.

BACKGROUND

Activin receptor-like kinase-2 (ALK2) is encoded by the Activin A receptor, type I gene (ACVR1). ALK2 is a serine/threonine kinase in the bone morphogenetic protein (BMP) pathway (Shore et al., Nature Genetics 2006, 38: 525-27). Inhibitors of ALK2 and mutant forms of ALK2 have the potential to treat a number of diseases, including fibrodysplasia ossificans progressiva (FOP); heterotopic ossification (HO) induced by, for example, major surgical interventions, trauma (such as head or blast injuries), protracted immobilization, or severe burns; diffuse intrinsic pontine glioma (DIPG), a rare form of brain cancer; and anemia associated with chronic inflammatory, infectious or neoplastic disease.

U.S. Pat. No. 10,233,186, the entire teachings of which are incorporated herein by reference, discloses potent, highly selective inhibitors of ALK2 and mutant forms of ALK2. Also disclosed in U.S. Pat. No. 10,233,186 is Compound 1 as a key intermediate in the Compound 1

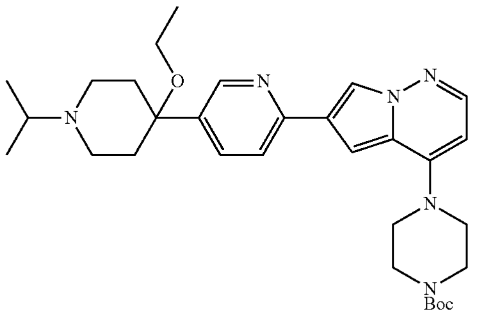

synthesis of many of the disclosed ALK2 inhibitors. U.S. Pat. No. 10,233,186 discloses Suzuki reactions for the preparation of intermediates such as Compound 1, as shown below:

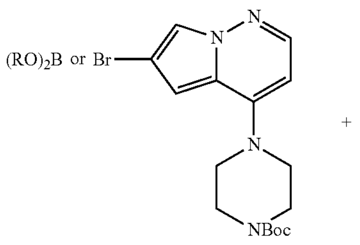

-continued

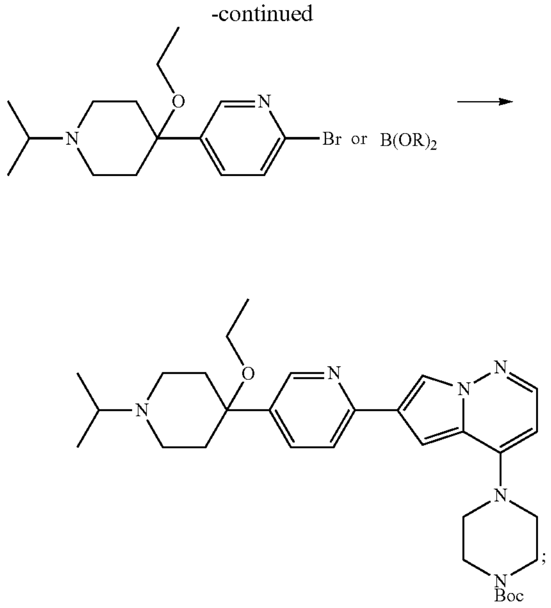

Compound 1 which involve the coupling of a pyrrolo-pyridazine intermediate with a piperidinyl-pyridine compound.

SUMMARY

It now has been found that the Suzuki coupling of 6-pyrrolo-pyridazine and the (bis(pinacolato)diboron piperidinyl-pyridine to prepare Compound 1 results in a complicated purity profile, whereas the formation of by-products in the corresponding Negishi coupling is considerably reduced (Example 5). The Negishi coupling has further advantages in that it requires smaller amounts of the expensive 6-pyrrolo-pyridazine starting material, has only one isolation step and uses inexpensive reagents ($ZnCl_2$ and i-propylmagnesiumchloride). Moreover, based on small scale reactions, it is expected that considerably higher yields will be obtained when the Negishi coupling is employed to prepare Compound 1 on an industrial scale than the Suzuki coupling. Based on these results, new and improved syntheses of important intermediate Compound 1 are disclosed.

In one embodiment, the disclosure provides a method of preparing a compound represented by formula (I):

(I)

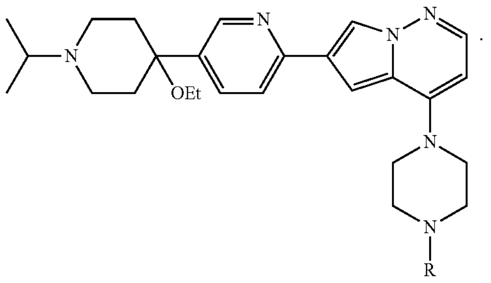

The method comprises reacting in a reaction mixture a first starting material represented by formula (II):

(II)

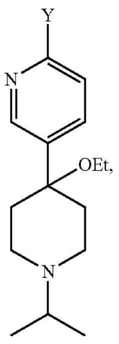

and a second starting material represented by formula (III) under Negishi conditions:

(III)

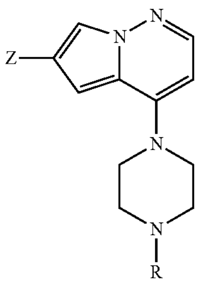

;

to form the compound of formula (I). R is an amine protecting group; Y is Cl, Br or I; and Z is Cl, Br, I or triflate (preferably Br). Amine protecting groups are well known in the art and are disclosed, for example, in T. W. Greene and P. G. M. Wuts "Protective Groups in Organic Synthesis" John Wiley & Sons, Inc., New York 1999. Protecting groups may be added and removed using methods well known in the art. Examples of amine protecting groups include (9-Fluorenylmethyl carbamate), Cbz (Benzyl carbamate), Boc (t-Butyl carbamate), acetamide, benzyl, tosyl (p-Toluenesulfonamide). In one embodiment, the amine protecting group is Boc.

Another embodiment of the present disclosure is a compound represented by formula (II), (II-A), or (II-B):

(II)

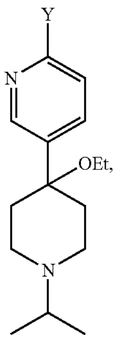

-continued (II-A)

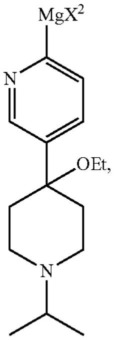

or (II-B)

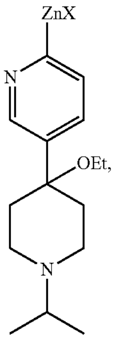

wherein Y, X, and $X^2$ are independently Cl, Br or I. In one embodiment, Y is Cl or I. The compounds represented by Formulas (II), (II-A) and (II-B) are intermediates in the disclosed Negishi Reaction, as described in greater detail below.

DETAILED DESCRIPTION

Figure 1:
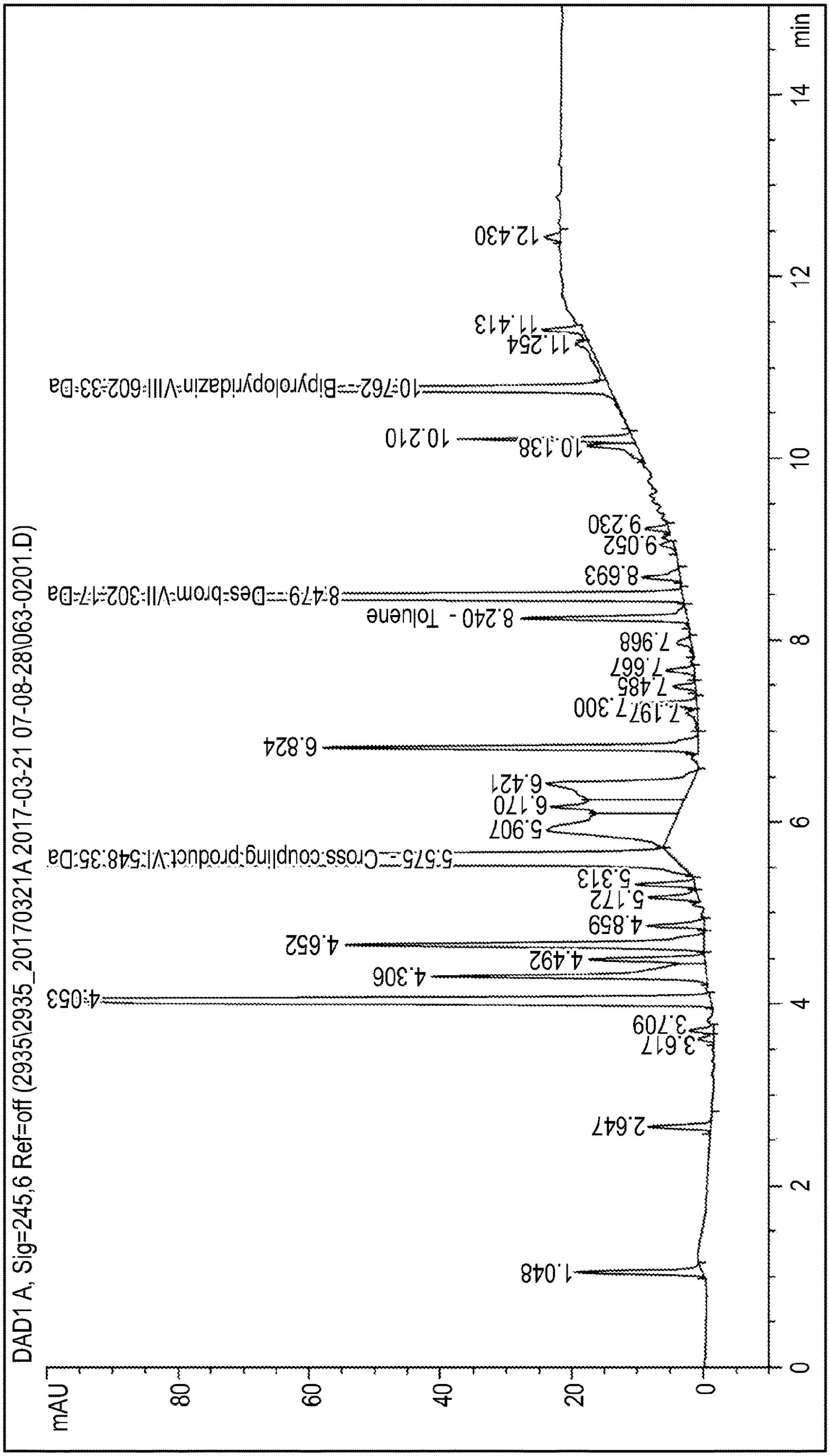
FIG. 1 is an ion pair chromatography (IPC) purity profile of the reaction product obtained from preparing Compound 1 by a Suzuki coupling as disclosed in U.S. Pat. No. 10,233,186.

The present disclosure provides an improved method for preparing Compound 1 in a good yield and a high purity via a Negishi Reaction (also referred to herein as a "Negishi Coupling").

The Negishi Reaction is a transition metal catalyzed cross-coupling reaction. The reaction couples organic halides or triflates with organozinc compounds, thereby forming carbon-carbon bonds (c-c) in the process. The transition metal catalyst is typically palladium or nickel. In the case of palladium, the catalytic species is Pd(0) in the form of, for example, $Pd(X^1)_2$; $X^1$ is a phosphine ligand. Alternatively, Pd(0) can be generated in situ from a $Pd^{+2}$ species in the form of, for example, $Pd(X^1)_2Cl_2$. Exemplary phosphine ligands include 1,1'-Bis(di-tert-butylphosphino)ferrocene (dtbpf), 1,1'-Bis(di-tert-butylphosphino)ferrocene (dcypf), 1,1'-Bis(diphenylphosphino)ferrocene (dppf), 2-Di-tert-butylphosphino-2',4',6'-triisopropylbiphenyl (t-BuXPhos), [2-(Di-1-adamantylphosphino)-2',4',6'-triisopropyl-3,6-dimethoxybiphenyl][2-(2'-amino-1,1'-biphenyl)]

palladium(II) methanesulfonate (AdBrettPhos), 2-Dicyclohexylphosphino-2',6'-dimethoxybiphenyl (SPhos), (2-Dicyclohexylphosphino-2',6'-diisopropoxy-1,1'-biphenyl)[2-(2'-amino-1,1'-biphenyl)]palladium(II) methanesulfonate (RuPhos), [2-Dicyclohexylphosphino-2',4',6'-triisopropylbiphenyl] (XPhos), [(2-Dicyclohexylphosphino-3,6-dimethoxy-2',4',6'-triisopropyl-1,1'-biphenyl)-2-(2'-amino-1,1'-biphenyl)]palladium(II) methanesulfonate methanesulfonate (BrettPhos), [(2-{Bis[3,5-bis(trifluoromethyl)phenyl]phosphine}-3,6-dimethoxy-2',4',6'-triisopropyl-1,1'-biphenyl)-2-(2'-amino-1,1'-biphenyl)] palladium(II) methanesulfonate (JackiePhos), [(2-Di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos), Mesyl(2-(di-tert-butylphosphino)-1,1'-binaphthyl)[2-(2'-amino-1,1'-biphenyl)]palladium (TrixiePhos), (2-Biphenyl)di-tert-butylphosphine, (2-Biphenylyl)di-tert-butylphosphine (JohnPhos), 2'-(Di-tert-butylphosphino)-N,N-dimethylbiphenyl-2-amine (t-BuDavePhos), 2-Di-tert-butylphosphino-2'-methylbiphenyl (t-BuMePhos), Chloro(2-dicyclohexylphosphino-1,1'-biphenyl)[2-(2'-amino-1,1'-biphenyl)]palladium(II) (CyJohnPhos), 2-Dicyclohexylphosphino-2'-(N,N-dimethylamino)biphenyl (DavePhos), 2-Dicyclohexylphosphino-2'-methylbiphenyl (MePhos), 2-Dicyclohexylphosphino-2'-(N,N-dimethylamino)biphenyl (PhDavePhos), 2-Dicyclohexylphosphino-2'-methoxy-4',6'-di-tert-butylbiphenyl (VPhos), 2-[(tert-Butyl)phenylphosphino]-2',6'-bis(N,N-dimethylamino)biphenyl. (PhCPhos), [(2-Dicyclohexylphosphino-2',6'-bis(N,N-dimethylamino)-1,1'-biphenyl)-2-(2'-amino-1,1'-biphenyl)] palladium(II) methanesulfonate (CPhos), Methanesulfonato[2-diethylphosphino-2',6'-bis(dimethylamino)-1,1-biphenyl](2'-amino-1,1'-biphenyl-2-yl) palladium(II) (EtCPhos), 2-Di(tert-butyl)phosphino-2',4',6'-triisopropyl-3-methoxy-6-methylbiphenyl (RockPhos), Di-1-adamantyl(4"-butyl-2",3",5",6"-tetrafluoro-2',4',6'-triisopropyl-2-methoxy-meta-terphenyl)phosphine (AlPhos) and 2-(t-Butylphenylphosphino)-2',6'-dimethylamino-1,1'-biphenyl, ((t-Bu)PhCPhos).

Exemplary palladium catalysts include $Pd(dppe)_2$ (Bis[1,2-bis(diphenylphosphino)ethane]palladium(0)), $Pd(dba)_2$ (Bis(dibenzylideneacetone)palladium(0)), CX-11 (1,3-Bis(2,6-diisopropylphenyl)imidazol-2-ylidene(1,4-naphthoquinone)palladium(0) dimer), CX-12 (1,3-Bis(2,4,6-trimethylphenyl)imidazol-2-ylidene(1,4-naphthoquinone) palladium(0) dimer), $Pd(t\text{-}Bu_3P)_2$ (Bis(tri-tert-butylphosphine)palladium(0)), $Pd(PCy_3)_2$ (Bis(tricyclohexylphosphine)palladium(0)), $Pd(PPh_3)_4$ (Tetrakis(triphenylphosphine)palladium(0)), $Pd_2(dba)_3$ (Tris(dibenzylideneacetone)dipalladium(0)), $Pd(OAc)_2$ (Palladium (II) acetate), $PdCl_2(PPh_3)_2$ (Dichlorobis(triphenylphosphine)palladium(II)), $PdCl_2(Amphos)_2$ (Bis(di-tert-butyl(4-dimethylaminophenyl)phosphine)dichloropalladium(II)), $Pd(MeCN)_2Cl_2$ (Bis(acetonitrile)dichloropalladium(II)), $PdCl_2(P(o\text{-}Tol)_3)_2$ (Dichlorobis(tri-o-tolylphosphine)palladium(II)), $Pd(dppf)Cl_2$ (1,1'-Bis(diphenylphosphino)ferrocene]dichloropalladium(II)), $Pd(MeCN)_4(BF_4)_2$ (Tetrakis(acetonitrile)palladium(II) tetrafluoroborate), Pd-PEPPSI-IPent (Dichloro[1,3-bis(2,6-Di-3-pentylphenyl)imidazol-2-ylidene](3-chloropyridyl)palladium(II)), Pd-PEPPSI-IPr ([1,3-Bis(2,6-Diisopropylphenyl)imidazol-2-ylidene](3-chloropyridyl)palladium(II) dichloride) and Pd-PEPPSI-SIPr ((1,3-Bis(2,6-Diisopropylphenyl)imidazolidene) (3-chloropyridyl) palladium(II) dichloride).

Alternatively, the palladium catalyst is selected from $Pd(MeCN)_2Cl_2$, $Pd[P(o\text{-}Tol)_3]_2Cl_2$, $PdCl_2(Amphos)_2$ and $Pd(dba)_2$. In another alternative, the palladium catalyst is selected from $Pd_2(dba)_3/P(R^1)_3$, $Pd(PPh_3)_4$, $Pd(PPh_3)_2Cl_2$, $Pd(MeCN)_2Cl_2$, $Pd[P(o\text{-}Tol)_3]_2Cl_2$, $PdCl_2(Amphos)_2$, $Pd(PtBu_3)_2$, $Pd(dppf)Cl_2$, $Pd(dba)_2$, $Pd_2(dba)_3$ and Pd(X-Phos); each $R^1$ is $C_1$-$C_6$ alkyl, $C_3$-$C_6$cycloalkyl, benzyl or phenyl and wherein the benzyl or phenyl is each optionally and independently substituted with one or more groups selected from halogen, $C_1$-$C_3$alkyl and $C_1$-$C_3$ alkoxy. In another alternative, the palladium catalyst is $Pd_2(dba)_3$. In yet another alternative, the palladium catalyst is $PdP(tBu)_3$.

In another embodiment, the palladium catalyst can be combined with a phosphine ligand, e.g., the palladium catalyst is $Pd_2(dba)$ combined with $P(tBu)_3$.

In the case of nickel, the catalytic species is Ni(0); and Ni(0) can be generated in situ from $Ni^{+2}$ species such as $NiCl_2$. Exemplary nickel catalyst include $Ni(acac)_2$, $Ni(cod)_2$, $Ni(PCy_3)2Cl2$, $NiBr_2$, $NiI_2$, $Ni(OAc)_2$, $Ni(OTf)_2$, $Ni(BF4)_2$, $NiCl_2(PPh_3)_2$.

The organic halide or organic triflate in the Negishi Reaction can be an alkenyl, aryl, allyl, alkynyl or propargyl halide or triflate; and the organozinc compound is R—Zn—X in which X is chloride, bromide or iodide and R is an alkenyl, aryl, allyl, alkyl, benzyl, homoallyl or homopropargyl group. Conditions for carrying out the Negishi Reaction are described in, for example, Recent Developments in Negishi Cross-Coupling Reactions Diana Haas, Jeffrey M. Hammann, Robert Greiner, Paul Knochel* *ACS Catal.* 2016, V6(3) p 1540-1552; Mild Negishi Cross-Coupling Reactions Catalyzed by Acenaphthoimidazolylidene Palladium Complexes at Low Catalyst Loadings Z. Liu, N. Dong, M. Xu, Z. Sun, T. Tu, *J. Org. Chem.,* 2013, 78, 7436-7444; An Extremely Active Catalyst for the Negishi Cross-Coupling Reaction J. E. Milne, S. L. Buchwald, *J. Am. Chem. Soc.,* 2004, 126, 13028-13032; One-Pot Negishi Cross-Coupling Reactions of In Situ Generated Zinc Reagents with Aryl Chlorides, Bromides, and Triflates S. Sase, M. Jaric, A. Metzger, V. Malakhov, P. Knochel, *J. Org. Chem.,* 2008, 73, 7380-7382; Efficient Negishi Coupling Reactions of Aryl Chlorides Catalyzed by Binuclear and Mononuclear Nickel-N-Heterocyclic Carbene Complexes Z. Xi, Y. Zhou, W. Chen, *J. Org. Chem.,* 2008, 73, 8497-8501; Cross-Coupling of Aryltrimethylammonium Iodides with Arylzinc Reagents Catalyzed by Amido Pincer Nickel Complexes X.-Q. Zhang, Z.-X. Wang, *J. Org. Chem.,* 2012, 77, 3658-3663; Efficient Cross-Coupling of Aryl Chlorides with Arylzinc Reagents Catalyzed by Amido Pincer Complexes of Nickel L. Wang, Z.-X. Wang, *Org. Lett.,* 2007, 9, 4335-4338; Highly Regio- and Stereoselective Synthesis of (Z)-Trisubstituted Alkenes via Propyne Bromoboration and Tandem Pd-Catalyzed Cross-Coupling C. Wang, T. Tobrman, Z. Xu, E.-i. Negishi, *Org. Lett.,* 2009, 11, 4092-4095; Highly Regioselective Synthesis of Trisubstituted Allenes via Lithiation of 1-Aryl-3-alkylpropadiene, Subsequent Transmetalation, and Pd-Catalyzed Negishi Coupling Reaction J. Zhao, Y. Liu, S. Ma, *Org. Lett.,* 2008, 10, 1521-1523; High Temperature Metalation of Functionalized Aromatics and Heteroaromatics using $(tmp)_2Zn\cdot 2MgCl_2\cdot 2LiCl$ and Microwave Irradiation S. Wunderlich, P. Knochel, *Org. Lett.,* 2008, 10, 4705-4707; A Mild Negishi Cross-Coupling of 2-Heterocyclic Organozinc Reagents and Aryl Chlorides M. R. Luzung, J. S. Patel, J. Yin, *J. Org. Chem.,* 2010, 75, 8330-8332; Synthesis of Substituted Cyclopropanecarboxylates via Room Temperature Palladium-Catalyzed α-Arylation of Reformatsky Reagents S. N. Greszler, G. T. Halvorsen, E. A. Voight, *Org. Lett.,* 2017, 19, 2490-2493; and Enantioselective, Palladium-Catalyzed α-Arylation of N-Boc-pyrrolidine K. R. Campos, A. Klapars, J. H. Waldman, P. G. Dormer, C.-Y. Chen, *J. Am. Chem. Soc.,* 2006, 128, 3538-3539.

Aryl zincs can be prepared using mild reaction conditions via a Grignard or organolithium intermediate with zinc metals such as $ZnCl_2$ or $ZnBr_2$. See, for example, Recent Developments in Negishi Cross-Coupling Reactions Diana Haas, Jeffrey M. Hammann, Robert Greiner, Paul Knochel* *ACS Catal.* 2016, V6(3) p 1540-1552. Giovannini R, Knochel P (1998). "*Ni(II)-Catalyzed Cross-Coupling between Polyfunctional Arylzinc Derivatives and Primary Alkyl Iodides". Journal of the American Chemical Society.* 120 (43): 11186-11187. doi:10.1021/ja982520o. Jie Jack Li, Chapter 3—Applications of Palladium Chemistry to the Total Synthesis of Naturally Occurring of Indole Alkaloids in "Alkaloids: Chemical and Biological Perspectives" 14:437-503 (1999). In some instances, the organozinc compound can be prepared directly by reacting with $ZnCl_2$. (S. P. Nolan and O. Navarro, 11.01—C—C Bond Formation by Cross-coupling in "Comprehensive Organometallic Chemistry III" 11:1-37 (2007).

The term "under Negishi conditions" means the transition metal catalyzed cross-coupling, carbon-carbon bond forming reaction between an organic halide and an organozinc compound. "Under Negishi conditions" also includes the formation of the organozinc compound, such as by reaction of a Grignard or oganolithium intermediate with a zinc halide.

In one aspect, i) the first starting material is converted into an organozinc intermediate represented by formula (II-B):

(II-B)

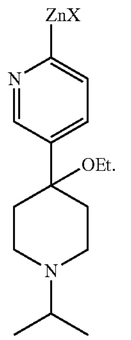

The organozinc intermediate is reacted with the second starting material in the presence of the palladium catalyst to form the compound of formula (I). X is Cl, Br or I. Alternatively, X in the organozinc intermediate (formula (II-B) is Cl; and Y in the second starting material (formula II) is Br. Suitable solvents for this reaction include ethereal solvents such as tetrahydrofuran, methyltetrahydrofuran, anisole and mixtures thereof. The organozinc intermediate is often reacted with the second starting material without isolation of the organozinc intermediate.

In one aspect, a solution of an alkoxide or amine base in an ethereal solvent is combined with the organozinc intermediate before reaction with the second starting material. Adding the base to the reaction mixture has the advantage of reducing by-product formation. Examples of suitable bases include potassium tert-butoxide (KOtBu), morpholine, piperazine, benzylpiperazine, $NH_3$, $NH_4Cl$, and hexamethyldisilazane. KOtBu is commonly used. In one aspect, between 0.5 and 3.0 equivalents of base relative to the first starting material. In one aspect, between 1.5 and 3.0 equivalents of base relative to the first starting material. Methyl tetrahydrofuran is a commonly used ethereal solvent.

In yet another aspect, the reaction with the organozinc intermediate and the second starting material is carried out in the presence of polar aprotic solvent such as N-methyl-2-pyrrolidinone, dimethylformamide or dimethyl sulfoxide. N-methyl-2-pyrrolidinone is commonly used. In one aspect, between 0.05 to 1.5 volumes or mL per gram starting material of the polar aprotic solvent are used.

In another aspect, the reaction mixture comprising the reaction product of the organozinc intermediate and the second starting material is extracted with a basic aqueous solution of N-acetyl-L-cysteine after formation of the compound of formula (I). The concentration of the N-acetyl-L-cysteine solution is generally less than 1 gram per 5 mL water. "Extraction" of the reaction mixture refers washing the reaction mixture directly with the N-acetyl-L-cysteine solution to form an aqueous phase and organic phase. The organic phase, which contains Compound 1, is then separated from the aqueous phase. Alternatively, "extraction" refers to quenching the reaction mixture with an aqueous solution to form an aqueous phase and organic phase. The organic phase, which contains Compound 1, is then separated from the aqueous phase, which is then extracted with the N-acetyl-L-cysteine solution. The N-acetyl-L-cysteine solution extraction has the advantage of reducing residual palladium in the final reaction product (Compound 1).

In another aspect, the organozinc intermediate is obtained by reacting the first starting material with a Grignard reagent $R'MgX^2$, to form an organometallic intermediate represented by formula (II-A):

(II-A)

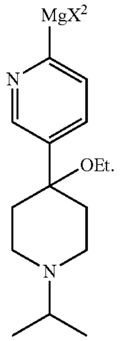

The organometallic intermediate is then reacted with $ZnX_2$ to form the organozinc intermediate. R' is a $C_1$-$C_6$ alkyl, $C_1$-$C_6$ alkenyl, $C_1$-$C_6$ alkynyl, phenyl, benzyl or monocyclic heteroaryl; the phenyl, benzyl or heteroaryl is each optionally and independently substituted with one or more groups selected from halogen, $C_1$-$C_3$alkyl and $C_1$-$C_3$ alkoxy group; and $X^2$ is Cl, Br or I. In one aspect, the Grignard reagent is iso-propyl magnesium chloride (i-PrMgCl). Conveniently, the organometallic intermediate is reacted with $ZnX_2$ without isolation of the organometallic intermediate.

The reaction of the first starting material with the Grignard reagent can be carried out in ethereal solvents. One commonly used ethereal solvent is tetrahydrofuran. In one aspect, the reaction of the first starting material with the Grignard reagent is carried out in a mixture comprising anisole and an ethereal solvent. Utilizing anisole in the reaction mixture has the advantage of reducing by-products. In one aspect, the reaction of the first starting material with the Grignard reagent is carried out in a mixture comprising an aromatic solvent such as benzene, toluene, xylene, and a mixture thereof.

Specific conditions for preparing Compound 1 by the methods of the present disclosure are provided in Examples 1 and 5. Compound 1 can be readily converted into ALK-2 inhibitors by first removing the amine protecting group and then carbamoylating the resulting free amine into the desired ALK-2 inhibitor. Suitable conditions for these two transformations are disclosed in U.S. Pat. No. 10,233,186. Specific conditions for the removal of a Boc protecting group are provided in Example 2 below; and in Examiner 3 for the carbamoylation.

The following examples are intended to be illustrative and are not intended to be limiting in any way to the scope of the disclosure.

EXEMPLIFICATION

Example 1 Preparation of tert-Butyl 4-(6-(5-(4-Ethoxy-1-Isopropylpiperidin-4-yl)Pyridin-2-yl)pyrrolo[1,2-b]Pyridazin-4-yl)Piperazine-1-Carboxylate

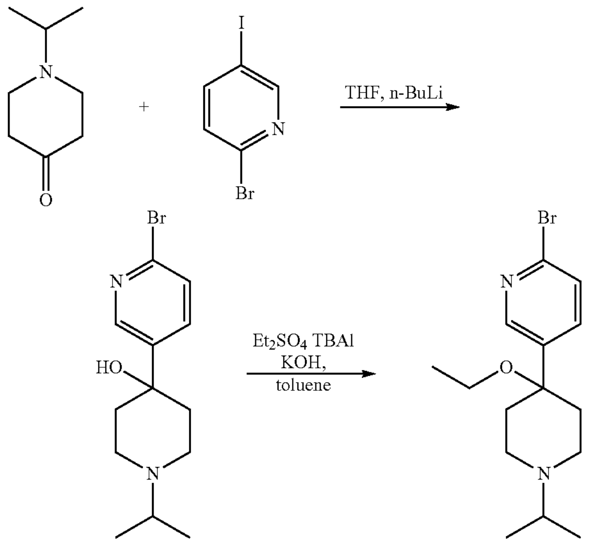

Compound 2

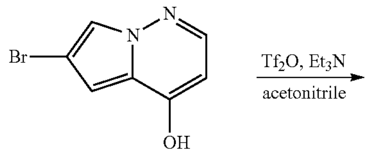

SM1

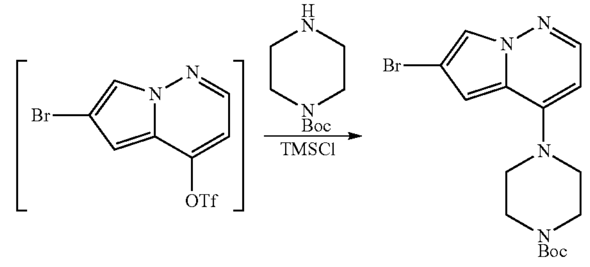

Compound 3

-continued

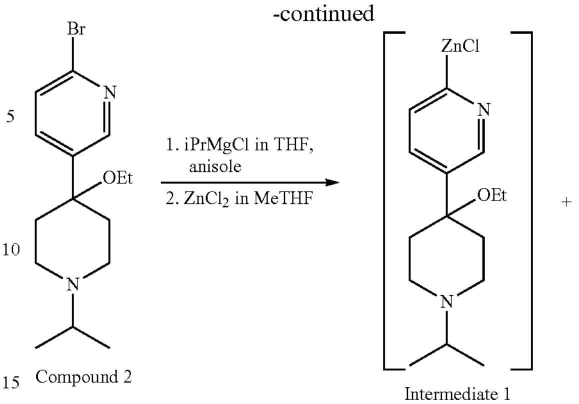

Compound 2

Intermediate 1

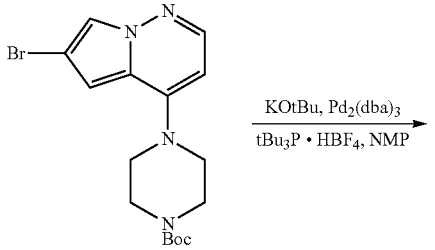

Compound 3

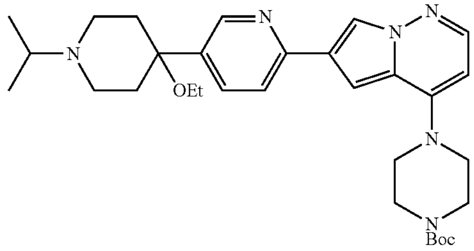

Compound 1

1.1 Preparation of 2-bromo-5-(4-ethoxy-1-isopropylpiperidin-4-yl)pyridine (Compound 2)

Compound 2 was prepared from starting materials 1-isopropylpiperidin-4-one and 2-bromo-5-iodopyridine via a synthetic route as shown in the scheme above. It was also commercially available from Acceledev.

1.2 Preparation of tert-butyl 4-(6-bromopyrrolo[1,2-b]pyridazin-4-yl)piperazine-1-carboxylate (Compound 3)

A mixture of 6-bromopyrrolo[1,2-b]pyridazine-4-ol (5.5 kg, 25.8 mol) and triethylamine (3.1 kg, 1.2 equiv) in acetonitrile (27 L, 4.9 volumes) is agitated at −10° C. To this mixture was added trifluoromethanesulfonic anhydride (7.1 kg, 0.98 equiv) with an additional rinse of acetonitrile (2 L, 0.36 volumes). The reaction was agitated until reaction completion, at which time trimethylsilyl chloride (0.3 kg, 0.1 equiv) is added. To the mixture is then added, triethylamine (3.7 kg, 1.3 equiv) and N-Boc-piperazine (5.5 kg, 1.2 equiv) with additional acetonitrile rinses (2 L, 0.36 volumes). The reaction was heated to 65-75° C. until reaction completion. The reaction mixture was concentrated at 45-55° C. and diluted with water before cooling to 15-25° C. to crystalize the product. The product was filtered and washed with isopropanol (2×11 L, 2×2 volumes) to give 7.0 kg (72.4% yield).

1.3 Preparation of tert-Butyl 4-(6-(5-(4-Ethoxy-1-Isopropylpiperidin-4-yl)Pyridin-2-yl)pyrrolo [1,2-b] Pyridazin-4-yl)Piperazine-1-Carboxylate (Compound 1)

2-Bromo-5-(4-ethoxy-1-isopropylpiperidin-4-yl)pyridine (Compound 2, 5.9 kg, prepared as disclosed in U.S. Pat. No. 10,233,186) was dissolved in anisole (24 L). The resulting solution was heated to 90-100° C. and partially distilled to lower water content. The remaining reaction solution was cooled to 45-55° C. and isopropylmagnesium chloride (20% in tetrahydrofuran, 9.6 kg) was added. Once complete conversion was observed a solution of zinc chloride (25% in methyltetrahydrofuran, 10.7 kg) was added while continuing heating. The resulting zinc organyl (Intermediate 1) solution was then charged with potassium tert-butoxide (25% in methyltetrahydrofuran, 17.6 kg), $Pd_2(dba)_3$ (18 g) and tert-$Bu_3P$•$HBF_4$ (23 g). Additionally, N-methyl-2-pyrrolidone (0.6 L) was added followed by tert-butyl 4-(6-bromopyrrolo [1,2-b]pyridazin-4-yl)piperazine-1-carboxylate (Compound 3, prepared as disclosed in U.S. Pat. No. 10,233,186) as a solution in tetrahydrofuran (6.0 Kg Compound 3 in 9 L of tetrahydrofuran). Heating was continued until complete conversion to Compound 1.

-continued

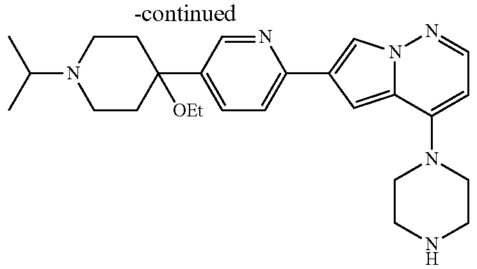

Compound 4

Compound 1 prepared as described in Example 1 was used without purification or isolation from the reaction mixture. The reaction mixture was diluted with tetrahydrofuran (8.8 kg) and 33% hydrochloric acid (21 kg) in water (36 kg) was added. The acidic aqueous mixture containing the product was washed with methyltetrahydrofuran (31 kg) and then isopropyl acetate (2×11 kg). The aqueous solution was then diluted with isopropyl acetate (53 kg) and basified with ammonia (25%, 33 kg). The organic phase was separated and washed with acetylcysteine (3×26 kg) and water (2×18 kg). The organic solution was seeded and heptane (41.7 kg) was added to crystalize the product that was then isolated by filtration to give approximately 3.6 kg of Compound 4 after drying.

Example 3 Preparation of ALK-2 Inhibitor from Compound 4

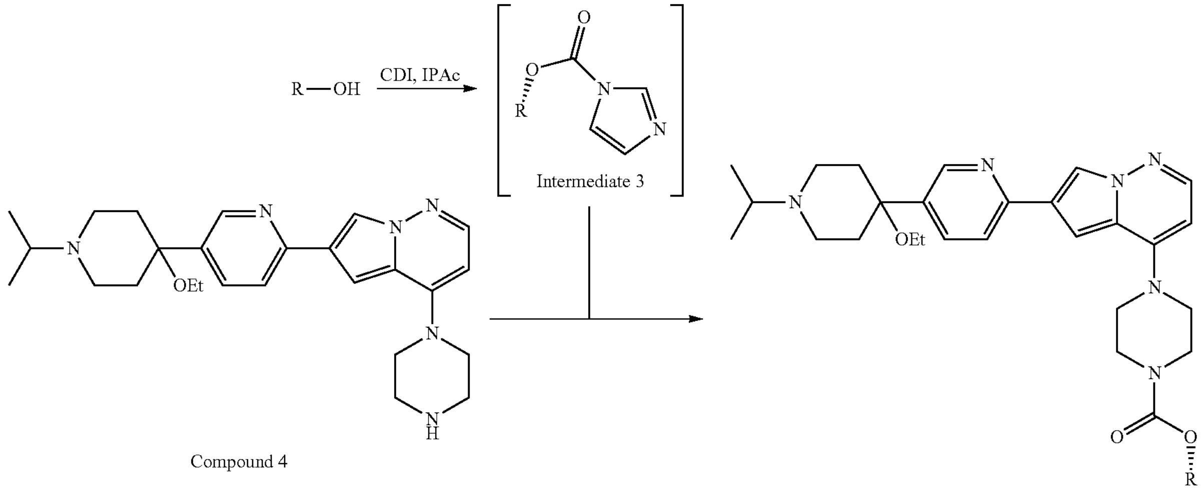

Example 2 Preparation of 6-(5-(4-ethoxy-1-isopropylpiperidin-4-yl)pyridin-2-yl)-4-(piperazin-1-yl) pyrrolo[1,2-b]pyridazine (Compound 4)

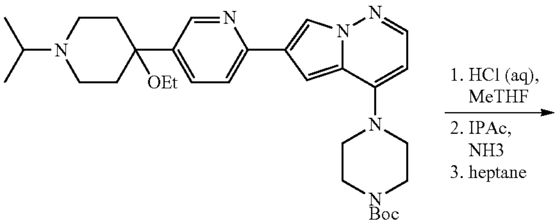

Compound 1

To the reactor was added 1,1-carbonyldiimidazol (1.51 kg), isopropyl acetate (6.4 kg), and the alcohol R—OH (e.g., 1.1 equivalents relative to 1,1-carbonyldiimidazol). The reaction was agitated 30 minutes at 20-30° C. until reaction completion. The reaction was heated to 30-40° C. and filtered, washing the filter with isopropyl acetate (7.7 kg). This diluted mixture was charged with ammonia (25%, 3.2 kg) and Compound 4 (3.5 kg) was added. The reaction was heated to 50-60° C. and distilled under vacuum. The mixture was further diluted with isopropyl acetate (6.1 kg) and reaction completion confirmed. At this time, the reaction mixture was diluted with water (3.5 kg) and isopropyl acetate (36.9 kg) and agitated. The mixture was allowed to settle, and organic phase separated. The organic solution was further washed with water (5×7 kg). The organic phase after final separation was diluted with isopropyl acetate (7.7 kg)

and distilled at 50-60° C. under vacuum to reduce the water content. The organic solvent can then be removed to isolate the ALK-2 inhibitor.

Example 4 N-Acetylcysteine is Significantly More Effective at Removing Palladium from the Reaction from Example 1 than Potassium Carbonate and 2,4,6-Trimercapto1,3,5-Triazine (TMT)

To 1.15 equivalents 2-bromo-5-(4-ethoxy-1-isopropylpiperidin-4-yl)pyridine (Compound 2) were added 6 volumes toluene and the mixture was heated to jacket temperature (JT) 145° C.[1]. At internal temperature (IT) 112-121° C. 4 volumes toluene were distilled. At IT 45° C. 1.37 equivalents iso-propyl magnesium chloride (2 M in tetrahydrofuran) were added in total to reach reaction completion. At that time, 1.20 equivalents $ZnCl_2$ (2 M in tetrahydrofuran) was added at 45° C. and the mixture was stirred at JT 80° C. for 14 hours. At IT 45° C. were added 0.1 volumes N-methyl-2-pyrroldinone, 1 mol % $Pd_2(dba)_3$, 4 mol % $tBu_3P{\bullet}HBF_4$. A solution of 1.0 equivalents Compound 3 (30.4 g) in 2.5 volumes methyltetrahydrofuran (MeTHF) was added over 30 minutes at IT 45° C. After 1 h additional 0.15 equivalents Compound 3 in 0.4 volumes tetrahydrofuran was added. The mixture was stirred for 2 hours at IT 45° C., transferred to another reaction vessel, rinsed with 1.6 volumes MeTHF and then added over 10 minutes to a solution of 4.1 equivalents $K_2CO_3$ in 25 volumes water at 24° C. Then, 0.43 volumes 30%-w/w NaOH were added, the aq. phase was separated and the organic phase split into three portions. Each portion was washed with 2×1.6 volumes of either (i) potassium carbonate, (ii) 2,4,6-trimercapto-1,3,5-triazine (TMT), or (iii) N-acetylcysteine. Then 3.3 volumes water and 0.95 volumes 2 M HCl were added and the organic phase was separated. Subsequently 0.30 volumes 30%-w/w NaOH and Norit CGP super (approx. 0.5 g) were added. The mixture was stirred at IT 45° C. for 2 hours, filtered, and washed with 0.33 volumes MeTHF. The organic phase was washed with 2×1 volumes water. $Boc_2O$ (0.08 vol, 2 M) was added and the mixture was stirred for 15 minutes at 24° C. MeTHF was distilled at JT 80-120° C. while n-heptane was added (3×1.6 volumes). The brown slurry was cooled to 0° C., stirred for 15 minutes, filtered, and washed with 2×0.7 volumes n-heptane (re-slurry washings).

[1] Equivalents and volumes are all relative to Compound 3, in which one equivalent is 30.4 g. Volume is 1 mL/1 gram of reference material, in this case Compound 3.

The quenched reaction mixture split into three portions and the palladium content determined by inductively coupled plasma mass spectrometry (IPC-MS) to be: Reference ($K_2CO_3$): 1'400 ppm Pd; 2× extraction with TMT: 1'000 ppm Pd; and 2× extraction with N-acetylcysteine: 120 ppm Pd.

Example 5 Negishi Process for Preparing Compound 1 Yields a Product with Fewer Impurities than the Corresponding Suzuki Process

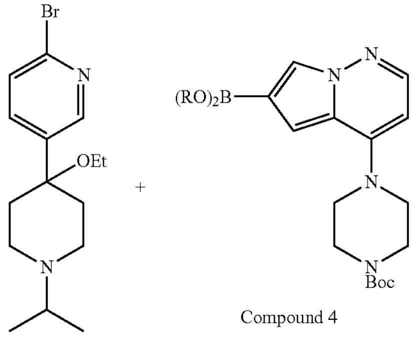

Compound 2 + Compound 4 Versus

Suzuki

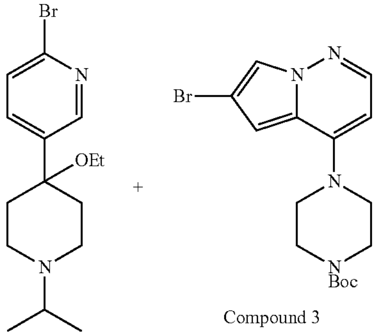

Compound 2 + Compound 3

Negishi

To a vessel containing Compound 4 (1.0 g) in water 2.4 mL (2.4 vol) and 1,4-dioxane (12.0 mL, 12 vol) was added 0.68 g (1.0 eq) of 2-bromo-5-(4-ethoxy-1-isopropylpiperidin-4-yl)pyridine (Compound 2), $K_2CO_3$ (0.57 g, 2.0 eq), and $Pd(PPh_3)_4$ (0.12 g, 0.05 eq). The reaction was heated to 80° C. until reaction completion was observed by HPLC (FIG. 1).

To 3.27 g of 2-bromo-5-(4-ethoxy-1-isopropylpiperidin-4-yl)pyridine (Compound 2) was added 6 vol toluene and 1.2 eq iPrMgCl (2 M in THF). The mixture was heated to JT 65° C. After reaching reaction completion, 1.3 eq $ZnCl_2$ (1.9 M in MeTHF) was added and the reaction held at 20-25° C. At 45° C., Compound 3 was added with $PdP(tBu_3)_2$ (0.1 eq) with THF (3 vol) and the mixture agitated until reaction completion by HPLC (FIG. 2).

Figure 2:
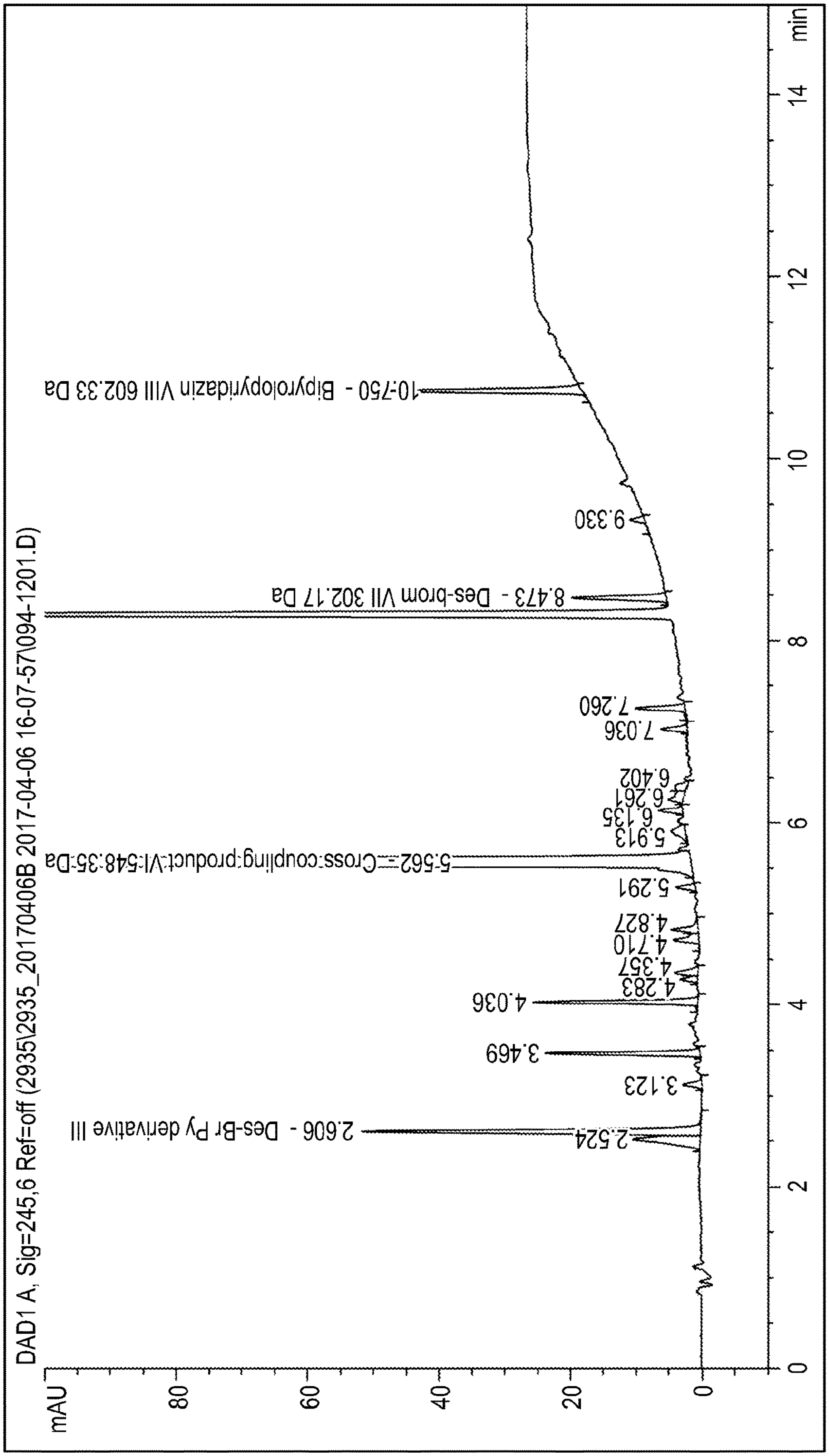
FIG. 2 is an IPC purity profile of the reaction product obtained from preparing Compound 1 by the method of the present disclosure, i.e., a Negishi Coupling.

It is evident from FIGS. 1 and 2 that the preparation of Compound 1 by the method of the present disclosure is considerably cleaner and produces far fewer impurities than the corresponding Suzuki coupling.

What is claimed is:

1. A method of preparing a compound represented by formula (I):

(I)

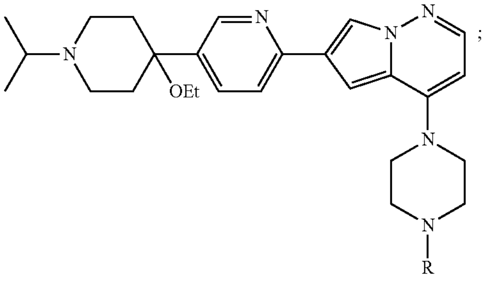

comprising reacting in a reaction mixture a first starting material represented by formula (II):

(II)

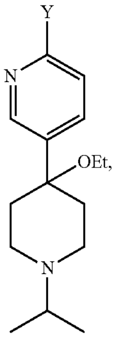

and a second starting material represented by formula (III) under Negishi conditions:

(III)

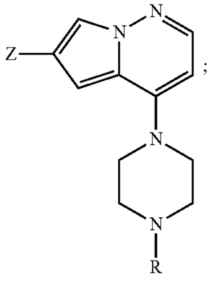

to form the compound of formula (I), wherein R is an amine protecting group; Y is Cl, Br or I; and Z is Cl, Br, I or triflate.

2. The method of claim 1, wherein the reaction is mediated by a palladium catalyst.

3. The method of claim 2, wherein:

i) the first starting material of formula (II) is converted into an organozinc intermediate represented by formula (II-B):

(II-B)

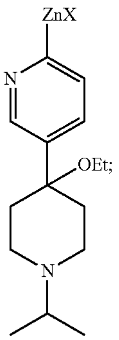

and ii) the organozinc intermediate of formula (II-B) is reacted with the second starting material of formula (III) in the presence of the palladium catalyst to form the compound of formula (I), wherein X is Cl, Br or I.

4. The method of claim 3, wherein X is Cl and Y is Br.

5. The method of claim 3, wherein the organozinc intermediate of formula (II-B) is reacted with the second starting material of formula (III) without isolation of the organozinc intermediate of formula (II-B).

6. The method of claim 2, wherein the palladium catalyst is selected from $Pd(X^1)_2$ and $Pd(X^1)_2Cl_2$, wherein each $X^1$ is independently a phosphine ligand.

7. The method of claim 2, wherein the phosphine ligand is selected from dtbpf, dcypf, dppf, t-BuXPhos, AdBrettPhos, SPhos, RuPhos, XPhos, BrettPhos, JackiePhos, t-BuBrettPhos, TrixiePhos, JohnPhos, t-BuDavePhos, t-BuMePhos, CyJohnPhos, DavePhos, MePhos, PhDavePhos, VPhos, PhCPhos, CPhos, EtCPhos, RockPhos, AlPhos and (t-Bu) PhCPhos.

8. The method of claim 2, wherein the palladium catalyst is selected from $Pd(dppe)_2$ (Bis[1,2-bis(diphenylphosphino)ethane]palladium(0)), $Pd(dba)_2$ (Bis(dibenzylideneacetone)palladium (0)), CX-11 (1,3-Bis(2,6-diisopropylphenyl)imidazol-2-ylidene(1,4-naphthoquinone)palladium(0) dimer), CX-12 (1,3-Bis(2,4,6-trimethylphenyl)imidazol-2-ylidene(1,4-naphthoquinone)palladium(0) dimer), $Pd(t\text{-}Bu_3P)_2$ (Bis(tri-tert-butylphosphine)palladium(0)), $Pd(PCy_3)_2$ (Bis(tricyclohexylphosphine)palladium(0)), $Pd(PPh_3)_4$ (Tetrakis(triphenylphosphine)palladium(0)), $Pd_2(dba)_3$ (Tris(dibenzylideneacetone)dipalladium(0)), $Pd(OAc)_2$ (Palladium (II) acetate), $PdCl_2(PPh_3)_2$ (Dichlorobis(triphenylphosphine)palladium(II)), $PdCl_2(Amphos)_2$ (Bis(di-tert-butyl (4-dimethylaminophenyl)phosphine)dichloropalladium(II)), $Pd(MeCN)_2Cl_2$ (Bis(acetonitrile)dichloropalladium(II)), $PdCl_2(P(o\text{-}Tol)_3)_2$ (Dichlorobis(tri-o-tolylphosphine)palladium(II)), $Pd(dppf)Cl_2$ (1,1'-Bis(diphenylphosphino)ferrocene]dichloropalladium(II)), $Pd(MeCN)_4(BF_4)_2$ (Tetrakis(acetonitrile)palladium(II) tetrafluoroborate), Pd-PEPPSI-IPent (Dichloro[1,3-bis(2,6-Di-3-pentylphenyl)imidazol-2-ylidene](3-chloropyridyl)palladium (II)), Pd-PEPPSI-IPr ([1,3-Bis(2,6-Diisopropylphenyl)imidazol-2-ylidene](3-chloropyridyl)palladium(II) dichloride), and Pd-PEPPSI-SIPr ((1,3-Bis(2,6-Diisopropylphenyl)imidazolidene) (3-chloropyridyl) palladium(II) dichloride).

9. The method of claim 2, wherein the palladium catalyst is selected from Pd $(MeCN)_2Cl_2$, $Pd[P(o\text{-}Tol)_3]_2Cl_2$, $PdCl_2(Amphos)_2$ and $Pd(dba)_2$.

10. The method of claim 2, wherein the palladium catalyst is selected from $Pd_2(dba)_3/P(R^1)_3$, $Pd(PPh_3)_4$, $Pd(PPh_3)_2Cl_2$, $Pd(MeCN)_2Cl_2$, $Pd[P(o\text{-}Tol)_3]_2Cl_2$, $PdCl_2(Amphos)_2$, $Pd(PtBu_3)_2$, Pd(dppf) $Cl_2$, $Pd(dba)_2$, $Pd_2(dba)_3$ and Pd(X-Phos), wherein each $R^1$ is $C_1$-$C_6$ alkyl, $C_3$-$C_6$cycloalkyl, benzyl or phenyl and wherein the benzyl or phenyl is each optionally and independently substituted with one or more groups selected from halogen, $C_1$-$C_3$alkyl and $C_1$-$C_3$ alkoxy.

11. The method of claim 2, wherein the palladium catalyst is $Pd_2(dba)_3$.

12. The method of claim 2, wherein the palladium catalyst is $PdP(tBu)_3$.

13. The method of claim 2, wherein the first starting material of formula (II) is converted into the organozinc intermediate of formula (II-B) by reacting the first starting material of formula (II) with a Grignard reagent $R'MgX^2$, to form an organometallic intermediate represented by formula (II-A):

(II-A)

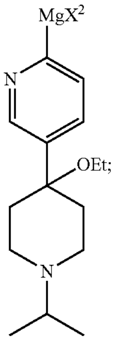

and the organometallic intermediate of formula (II-A) is reacted with $ZnX_2$ to form the organozinc intermediate of formula (II-B), wherein R' is a $C_1$-$C_6$ alkyl, $C_2$-$C_6$ alkenyl, $C_2$-$C_6$ alkynyl, phenyl, benzyl or monocyclic heteroaryl, wherein the phenyl, benzyl or heteroaryl is each optionally and independently substituted with one or more groups selected from halogen, $C_1$-$C_3$alkyl and $C_1$-$C_3$ alkoxy group and $X^2$ is Cl, Br or I.

14. The method of claim 13, wherein the Grignard reagent is i-PrMgCl.

15. The method of claim 13, wherein the organometallic intermediate of formula (II-A) is reacted with $ZnX_2$ without isolation of the organometallic intermediate of formula (II-A).

16. The method of claim 13, wherein the first starting material of formula (II) is reacted with the Grignard reagent in a mixture comprising anisole.

17. The method of claim 16, wherein the first starting material of formula (II) is reacted with the Grignard reagent in a mixture of anisole and an ethereal solvent.

18. The method of claim 17, wherein the ethereal solvent is tetrahydrofuran.

19. The method of claim 3, wherein KOtBu in an ethereal solvent is combined with the organozinc intermediate of formula (II-B) before reaction with the second starting material of formula (III).

20. The method of claim 19, wherein the organozinc intermediate of formula (II-B) is combined with KOtBu in tetrahydrofuran.

21. The method of claim 19, wherein the reaction of the organozinc intermediate of formula (II-B) and the second starting material of formula (III) is carried out in the presence N-methyl-2-pyrollidinone.

22. The method of claim 1, further comprising extracting the reaction mixture after formation of the compound of formula (I) with a basic aqueous solution of N-acetyl-L-cysteine.

23. The method of claim 1, wherein R is selected from Fmoc (9-Fluorenylmethyl carbamate), Cbz (Benzyl carbamate), Boc (tert-butoxycarbonyl), Acetamide, benzyl, tosyl (p-Toluenesulfonamide).

24. The method of claim 23, wherein R is tert-butoxycarbonyl.

25. The method of claim 1, wherein Z is Br.

26. The method of claim 13, wherein the first starting material of formula (II) is reacted with the Grignard reagent in a mixture comprising an aromatic solvent selected from the group consisting of benzene, toluene, and xylene.

27. A method of preparing a compound represented by formula (I):

(I)

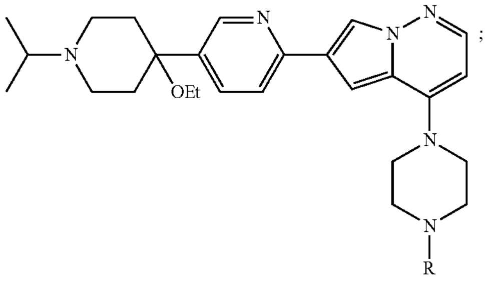

wherein R is Boc (tert-butoxycarbonyl);

comprising:

i) converting a first starting material represented by formula (II):

(II)

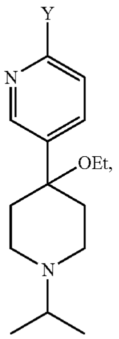

wherein Y is Br;

into an organozinc intermediate of formula (II-B) by reacting the first starting material of formula (II) with iPrMgCl in anisole and tetrahydrofuran, to form an organometallic intermediate represented by formula (II-A):

(II-A)

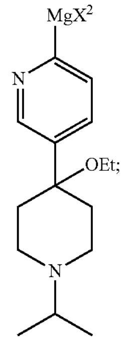

wherein $X^2$ is Cl;

followed by reacting the organometallic intermediate of formula (II-A) with $ZnCl_2$ in methyl tetrahydrofuran to form the organozinc intermediate represented by formula (II-B):

(II-B)

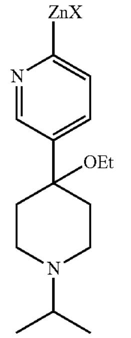

wherein X is Cl; and ii) reacting the organozinc intermediate of formula (II-B) with a second starting material represented by formula (III):

(III)

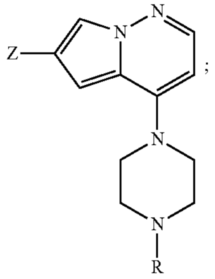

wherein R is Boc (tert-butoxycarbonyl) and Z is Br;

in the presence of the palladium catalyst to form the compound of formula (I); wherein the palladium catalyst is $Pd_2(dba)_3$, wherein the reaction further comprises $tBu_3P$—$HBF_4$, KotBu, and N-methyl-2-pyrollidinone.

* * * * *